United States Patent
Sheldon

(10) Patent No.: US 8,764,817 B2
(45) Date of Patent: Jul. 1, 2014

(54) METHODS FOR SECURING STRANDS OF WOVEN MEDICAL DEVICES AND DEVICES FORMED THEREBY

(75) Inventor: Jeffery J. Sheldon, Friendswood, TX (US)

(73) Assignee: IDEV Technologies, Inc., Webster, TX (US)

( * ) Notice: Subject to any disclaimer, the term of this patent is extended or adjusted under 35 U.S.C. 154(b) by 641 days.

(21) Appl. No.: 10/092,385

(22) Filed: Mar. 5, 2002

(65) Prior Publication Data

US 2002/0151933 A1 Oct. 17, 2002

Related U.S. Application Data

(60) Provisional application No. 60/273,586, filed on Mar. 5, 2001.

(51) Int. Cl.
*A61F 2/90* (2013.01)
(52) U.S. Cl.
USPC ....... 623/1.51; 623/1.1; 623/1.15; 623/11.11; 606/151
(58) Field of Classification Search
USPC ................ 43/9.95, 9.8; 289/1.5, 1.2; 256/33; 623/1.15, 1.16, 1.32, 1.49, 1.1, 11.11; 606/151, 191, 200, 228
See application file for complete search history.

(56) References Cited

U.S. PATENT DOCUMENTS

| | | | |
|---|---|---|---|
| 619,403 A | 10/1898 | Grant et al. | |
| 1,947,166 A * | 2/1934 | Nydegger | 174/34 |
| 2,162,115 A * | 10/1938 | Pauls | 289/1.5 |
| 4,003,289 A * | 1/1977 | Yamashita | 87/12 |
| 4,081,885 A * | 4/1978 | Shank | 28/149 |
| 4,469,101 A * | 9/1984 | Coleman et al. | 606/151 |
| 4,655,771 A | 4/1987 | Wallsten | 623/1 |
| 5,405,377 A * | 4/1995 | Cragg | 623/1.2 |
| 5,618,301 A | 4/1997 | Hauenstein et al. | 606/198 |
| 5,665,115 A * | 9/1997 | Cragg | 623/1.13 |
| 5,683,450 A * | 11/1997 | Goicoechea et al. | 606/194 |
| 5,716,365 A * | 2/1998 | Goicoechea et al. | 623/1.16 |
| 5,718,724 A * | 2/1998 | Goicoechea et al. | 606/194 |
| 5,766,237 A | 6/1998 | Cragg | 623/1 |
| 5,776,180 A * | 7/1998 | Goicoechea et al. | 606/36 |
| 5,800,508 A * | 9/1998 | Goicoechea et al. | 623/1.15 |
| 5,843,158 A * | 12/1998 | Lenker et al. | 623/1.13 |

(Continued)

OTHER PUBLICATIONS

The Ashley Book of Knots by Clifford Ashley, 1944. pp. 191, 338, 537, 541, 343, 346.*

(Continued)

*Primary Examiner* — Melanie Tyson
*Assistant Examiner* — Katelyn Bernier
(74) *Attorney, Agent, or Firm* — Fulbright & Jaworski LLP

(57) ABSTRACT

Disclosed are methods for securing the intersection formed by two or more crossed strands. The intersection defines at least two sections. The practice of the disclosed methods includes bending a securing material, such as a suture or other suitably biocompatible material, through at least two of the sections formed by the intersection, and joining them to secure the intersection. Also disclosed are devices formed by using securing material to secure the intersection of crossed strands of a medical device, such as a woven stent. The secured intersection or intersections of the resultant device enhance the structural integrity of the device, and may serve to eliminate the possible unwinding or release of unsecured, or free, strand ends. Radiopaque materials, in addition to polymers, may be used as securing material.

6 Claims, 4 Drawing Sheets

(56) References Cited

U.S. PATENT DOCUMENTS

| | | | |
|---|---|---|---|
| 5,873,906 A | 2/1999 | Lau et al. | 623/1 |
| 5,916,263 A * | 6/1999 | Goicoechea et al. | 623/1.11 |
| 5,938,696 A * | 8/1999 | Goicoechea et al. | 606/194 |
| 6,027,529 A * | 2/2000 | Roychowdhury et al. | 623/1.53 |
| 6,051,020 A * | 4/2000 | Goicoechea et al. | 623/1.35 |
| 6,063,113 A * | 5/2000 | Kavteladze et al. | 623/1.15 |
| 6,117,167 A * | 9/2000 | Goicoechea et al. | 623/1.16 |
| 6,123,115 A * | 9/2000 | Greenhalgh | 139/196.1 |
| 6,159,239 A * | 12/2000 | Greenhalgh | 623/1.13 |
| 6,164,339 A * | 12/2000 | Greenhalgh | 139/1 R |
| 6,165,213 A * | 12/2000 | Goicoechea et al. | 623/1.34 |
| 6,174,328 B1 * | 1/2001 | Cragg | 623/1.16 |
| 6,174,330 B1 * | 1/2001 | Stinson | 623/1.34 |
| 6,200,337 B1 | 3/2001 | Moriuchi et al. | 623/1.16 |
| 6,214,025 B1 * | 4/2001 | Thistle et al. | 606/200 |
| 6,251,135 B1 * | 6/2001 | Stinson et al. | 623/1.34 |
| 6,340,367 B1 * | 1/2002 | Stinson et al. | 623/1.34 |
| 6,350,277 B1 | 2/2002 | Kocur | 623/1.11 |
| 6,409,750 B1 | 6/2002 | Hyodoh et al. | 623/1.1 |
| 6,592,614 B2 * | 7/2003 | Lenker et al. | 623/1.13 |
| 6,626,936 B2 * | 9/2003 | Stinson | 623/1.15 |
| 6,786,919 B1 * | 9/2004 | Escano et al. | 623/1.13 |
| 6,849,086 B2 * | 2/2005 | Cragg | 623/1.13 |
| 6,881,221 B2 * | 4/2005 | Golds | 623/1.13 |

OTHER PUBLICATIONS

"How to Tie a Clove Hitch Knot," eHow, http://www.ehow.com/how_7532_tie-clove-hitch.html, pp. 1 and 2.*

"How to Tie a Bow-Tie," www.cam.ac.uk/societies/cuhags/whitetie/howtotie.htm: pp. 1-3.*

Co-pending U.S. Appl. No. 09/496,243 by Hideki Hyodoh et al., filed Feb. 1, 2000.

* cited by examiner

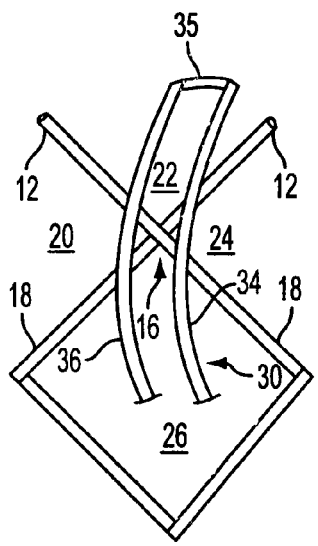
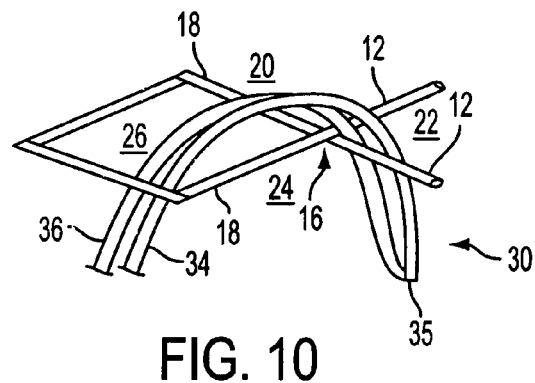
FIG. 9
FIG. 10
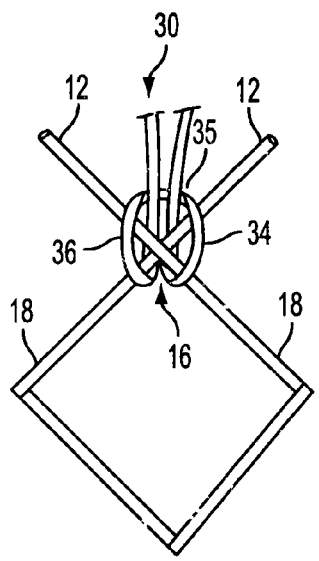
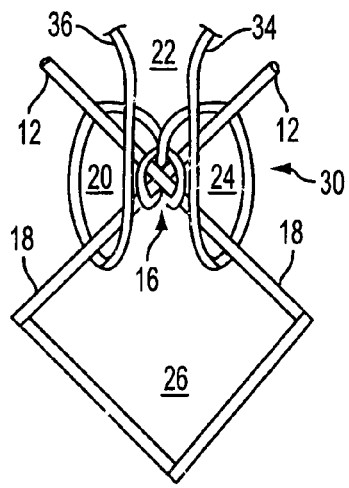
FIG. 11
FIG. 14

METHODS FOR SECURING STRANDS OF WOVEN MEDICAL DEVICES AND DEVICES FORMED THEREBY

This application claims priority to U.S. Provisional Patent Application Ser. No. 60/273,586, filed Mar. 5, 2001.

BACKGROUND OF THE INVENTION

1. Field of the Invention

The present invention relates to methods useful for securing intersections formed by crossed strands of medical devices, such as woven stents. More particularly, the present invention relates to methods that include the use of securing materials to secure intersections formed by crossed strands of medical devices, and the devices formed thereby.

2. Description of Related Art

Medical devices serve a variety of uses in the treatment of various vascular and non-vascular disorders. Stents are one example of such medical devices. A stent is a device that may be placed within an internal body structure, such as a blood vessel, to maintain the patency of the internal body structure. For example, when a blood vessel becomes weak and contracted due, for example, to disease and begins to collapse, a stent may be inserted into the blood vessel, placed at the weak or diseased location, and will serve to prop open the weak or diseased portion of the blood vessel in order to allow blood to continue flowing. Various graft materials may also be coupled to stents to form what some term stent grafts. These stents grafts may be thought of as woven frames that have biocompatible jackets coupled to the frames. When an internal body structure such as a blood vessel becomes weak and expands, thereby creating a conduit with a weak, ballooned-out segment, a stent graft may be placed across the ballooned-out segment in order to restore the proper flow of fluid through the body structure.

The types of medical devices just described are often woven out of strands of biocompatible material of some kind, as are certain metals. One such woven medical device, in particular a woven stent, is the subject of U.S. Pat. No. 4,655,771 to Wallsten (hereinafter "the Wallsten patent"), which is hereby expressly incorporated herein by reference. A version of the subject of this patent is marketed as the WALLSTENT, which is manufactured and sold by Boston Scientific Corporation. Other woven medical devices are disclosed in U.S. patent application Ser. No. 09/496,243, filed Feb. 1, 2000 and entitled "Woven Intravascular Devices and Methods For Making the Same and Apparatus for Delivery of the Same" (hereinafter "first patent application") and in U.S. patent application Ser. No. 09/495,984, filed Feb. 1, 2000 and entitled "Woven Bifurcated and Trifurcated Stents and Methods For Making the Same" (hereinafter "second patent application"), both of which are hereby expressly incorporated herein by reference. The ends of the strands of woven devices may be left free after the weaving process is complete. If delivered into an internal body structure, such as a blood vessel, in such a condition, the free strand ends may damage the internal body structure.

Different steps have been taken to secure the free strand ends of such woven devices. Some methods that have been used in this regard include securing free strand ends using laser welding, soldering, and brazing. These traditional methods may raise issues about material biocompatibility, and may cause problems such as loss of product structural integrity due to a change in material characteristics during the securing process, and the possible introduction of a foreign body into vessel should a piece of welding or soldering material break free. These problems are not intended to be exhaustive, but rather are among many that tend to impair the effectiveness of previously known methods of securing the free strand ends of certain woven medical devices. Other noteworthy problems may also exist; however, those presented above should be sufficient to demonstrate that previous techniques of securing the free strand ends, also described herein as securing the intersection formed by two or more crossed strands, of certain medical devices have not been altogether satisfactory.

SUMMARY OF THE INVENTION

In one respect, a method of securing an intersection formed from two or more crossed strands, in which the intersection defines at least two sections, is provided. The method includes passing a securing material through at least two of the at least two sections defined by the intersection. The passing includes bending the securing material at a location, thereby defining a securing material segment on each side of the location. The method also includes joining the two securing material segments to secure the intersection.

In other respects, the joining may include tying the two securing material segments. The securing material may include, for example, thread, nylon, metal, or wire. The securing material may be radio opaque. The method may also include gluing the securing material. The method may include heating the securing material. The method may also include cutting excess securing material. In one embodiment, each strand has a free end that extends away from the intersection; the free end of each strand and the intersection may define a strand segment having a length; and the method may include reducing the length of at least one of the strand segments.

In another respect, another method of securing an intersection formed from two or more crossed strands, in which the intersection defines at least two sections, is provided. The method includes bending a securing material, thereby forming a closed end and a securing material segment on each side of the closed end; passing the closed end through at least one of the at least two sections; passing both securing material segments through at least one of the at least two sections; and passing both securing material segments through the closed end to secure the intersection.

In other respects, the method may also include joining the securing material segments. The joining may include tying the two securing material segments. The securing material may include, for example, thread, nylon, metal, or wire. The securing material may be radio opaque. The method may also include gluing the securing material. The method may include heating the securing material. The method may also include cutting excess securing material. In one embodiment, each strand has a free end that extends away from the intersection; the free end of each strand and the intersection may define a strand segment having a length; and the method may include reducing the length of at least one of the strand segments. The method may further include passing each securing material segment at least twice through at least two of the at least two sections.

In still another respect, a device suitable for implantation into a living being is provided. The device includes a body having at least two strands crossed to form an intersection. The intersection defines at least two sections. The device also includes a securing material passed through at least two of the at least two sections. The securing material is bent at a location and has a securing material segment on each side of the location. The securing material segments are joined together.

BRIEF DESCRIPTION OF THE DRAWINGS

The following drawings form part of the present specification and are included to further demonstrate certain aspects of the present methods and devices. The present methods and devices may be better understood by reference to one or more of these drawings in combination with the description of illustrative embodiments presented herein. These drawings illustrate by way of example and not limitation, and they use like references to indicate similar elements. The drawings include:

FIG. 9 illustrates an embodiment of a securing material that is bent to form a closed end and two securing material segments in which both the closed end and the two securing material segments are passing through sections defined by two or more crossed strands.

FIG. 10 is a side view taken from a slight perspective of the intersection and securing material depicted in FIG. 9.

FIG. 11 depicts passing the securing material segments depicted in FIG. 9 through the closed end depicted in FIG. 9.

FIG. 14 depicts the securing material segments depicted in FIG. 11 as passing at least twice through at least two of the sections defined by the intersection shown.

DESCRIPTION OF ILLUSTRATIVE EMBODIMENTS

As a preliminary matter, it should be noted that as used herein, the terms "comprise" (and any form thereof, such as "comprises" and "comprising"), "have" (and any form thereof, such as "has" and "having"), and "include" (and any form thereof, such as "includes" and "including") are open-ended transitional terms, meaning that a device, a method, or a step in a method that "comprises," "has," or "includes" one or more elements or steps possesses those one or more elements or steps, but is not limited to those one or more elements or steps. Thus, and by way of example, a step of passing that includes bending a securing material at a location is a passing that has, but is not limited to, bending a securing material at a location. That is, the passing step in question possesses the recited step of bending, but does not exclude other steps or elements that are not expressly recited.

The present disclosure details devices created by and methods of securing intersections formed from two or more crossed strands that are part of vascular or non-vascular products. The present methods enhance the structural integrity of the devices in question, and may serve to eliminate the possible unwinding or release of unsecured, or free, strand ends. Depending on the securing material used, the present methods may be useful in increasing the radiopacity of the devices as well.

Figure 1:
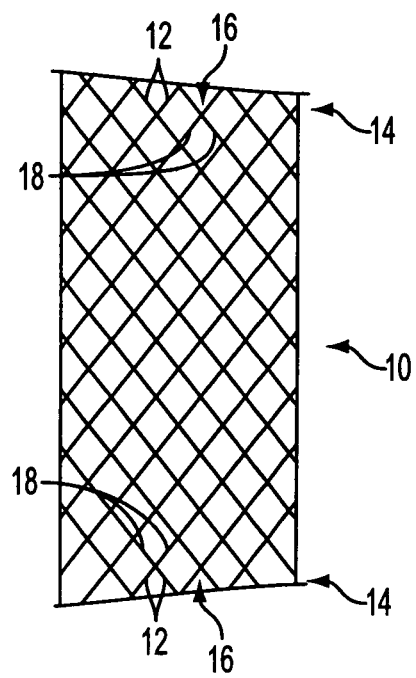
FIG. 1 is a front view of a conventionally woven medical device having free strand ends.

FIG. 1 illustrates a conventional woven stent 10, such as the WALLSTENT, which includes two ends 14, strands 18, free strand ends 12, and intersection 16 formed from at least two crossed strands 18. As used herein, a stent or other device that is "woven" may be formed using any weaving method disclosed in the Wallsten patent, the first patent application, or the second patent application. Further, strands need not be weaved from end to end of a device for the same to be "woven" as that term is used herein. Further, to the extent not disclosed in these three, the term "woven" as used herein includes all other weaves known to those of skill in the art that may be useful in forming medical devices. Additionally, as used herein, "two crossed strands" includes both two distinct strands that cross each other, as is the case with the strands disclosed in the Wallsten patent, and two portions of the same strand that cross each other, as may be the case with the strands disclosed in, for example, the first patent application. Further still, as used herein, "strands" include any suitably biocompatible materials, including certain polymers and metals.

Figure 2:
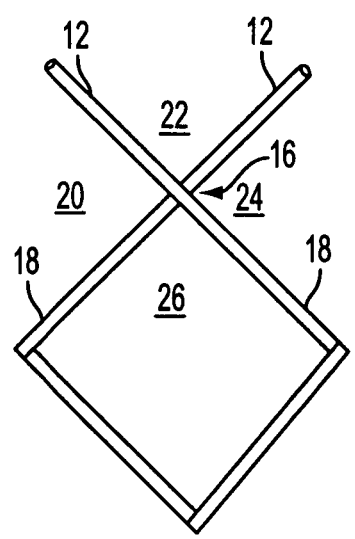
FIG. 2 is an enlarged view of the intersection of two strands near their free strand ends.

FIG. 2 illustrates an enlarged view of an intersection 16 formed by crossed strands 18 having free strand ends 12. Intersection 16 defines sections 20, 22, 24, and 26. Thus, intersection 16 may be said to define at least two sections. Moreover, intersection 16 may be said to define two pairs of opposing sections—sections 20 and 24, and sections 22 and 26.

Figure 3:
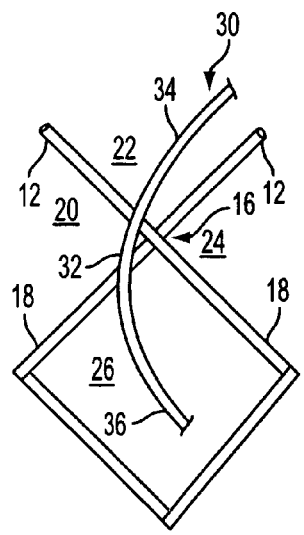
FIG. 3 illustrates one embodiment of a securing material passing through at least two of the sections defined by the intersection of two or more crossed strands.
Figure 4:
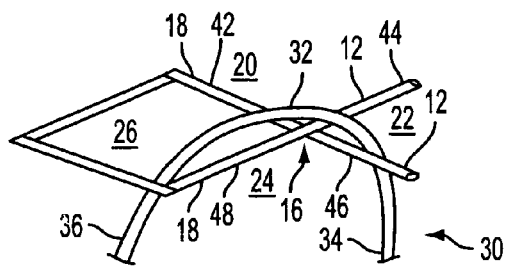
FIG. 4 is a side view taken from a slight perspective of the intersection and securing material depicted in FIG. 3.

FIGS. 3 and 4 illustrate one embodiment of a step that may be used as part of the present methods to create the present devices. Specifically, FIG. 3 illustrates the same enlarged version of the intersection 16 illustrated in FIG. 2. FIG. 3 further illustrates a securing material 30 that is passing through sections 22 and 26. Thus, it may be said that FIG. 3 illustrates securing material 30 passing through at least two (i.e., sections 22 and 26) of the at least two sections defined by intersection 16 (i.e., sections 20, 22, 24, and 26). As illustrated in FIG. 3, securing material 30 is bent at location 32, which thereby defines securing material segments 34 and 36 on each side of location 32. The length of securing material segments 34 and 36 varies, and the two need not always be equal. Such is the case for all securing material segments disclosed herein. It will be understood to those of skill in the art having the benefit of this disclosure that the view depicted in FIG. 3 may be characterized as being from the perspective of one looking either out through the lumen of a woven device (e.g., a stent) or into the lumen of the woven device.

FIG. 4 is a side view of the securing material and intersection depicted in FIG. 3, the side view being taken from a slight perspective. FIG. 4 is included to illustrate one embodiment of a securing material (i.e., securing material 30) passing through at least two sections (i.e., sections 22 and 26). As used herein, a securing material "passing through" a section breaks the plane formed by the strand portions that at least partially outline the section. As illustrated in FIG. 4, securing material 30 passing through section 22 breaks the plane formed by strand portions 44 and 46, which strand portions at least partially outline section 22. It will be understood by those skilled in the art having the benefit of this disclosure that rarely, if ever, will a strand portion be perfectly straight. In cases in which both strand portions at least partially outlining a section (e.g., strand portions 44 and 46 at least partially outlining section 22, and strand portions 42 and 48 at least partially outlining section 26) are perfectly straight, the plane formed thereby will be flat. In cases in which both strand portions at least partially outlining a section share the same curve, the plane formed thereby will be curved. However, should two strand portions at least partially outlining a section do not share the same curve or are not both straight, those strand portions cannot form a plane. Nevertheless, consistent with the manner in which the phrase "passing through" a section is used herein, a plane may be oriented with respect to the two strand portions in question such that volumes of the areas between the plane and the two strand portions (i.e., the area above the strand portions and below the plane, and the area above the plane and below the strand portions) will cancel each other out.

Figure 5:
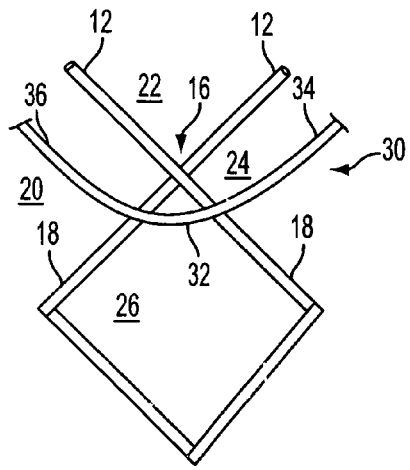
FIG. 5 illustrates another embodiment of a securing material passing through at least two of the sections defined by the intersection of two or more crossed strands.
Figure 6:
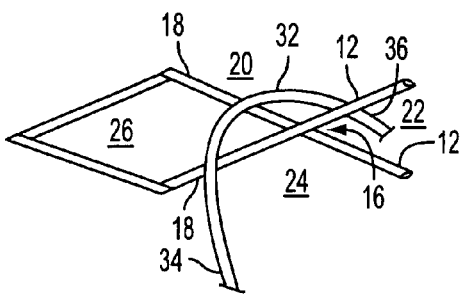
FIG. 6 is a side view taken from a slight perspective of the intersection and securing material depicted in FIG. 5.

FIGS. 5 and 6 depict an alternate embodiment of a securing material passing through at least two of the sections defined by an intersection. These figures are comparable in terms of the view depicted to FIGS. 3 and 4. Specifically, FIG. 5 depicts securing material 30 passing through sections 20 and 24, which are at least two sections defined by intersection 16. Further, FIG. 6 depicts a side view of the securing material and intersection depicted in FIG. 5, the side view being taken from a slight perspective.

In accordance with the present methods, and in the case of any of the embodiments disclosed herein, after a securing material passes through at least two sections, the securing material segments may be joined in any suitable fashion. For example, the securing material segments of a securing material may be joined by tying the securing material segments together. Any suitable knot may be used in this regard. Such knots include square knots, surgeon's knots, square slip knots, and granny knots, to name but a few. In embodiments in which the intersections formed by two or more crossed strands of a stent or other medical device having a lumen (i.e., a passageway therethrough) are secured, the joining may be such that the joined securing material may be partially or completely oriented outside the flow path, or lumen. Such an arrangement may prove to improve the viability of the device in question. It will be understood, however, by those of skill in the art having the benefit of this disclosure that, in certain circumstances, the joined securing material may also be oriented within the flow path, or lumen, of a given device.

Figure 7:
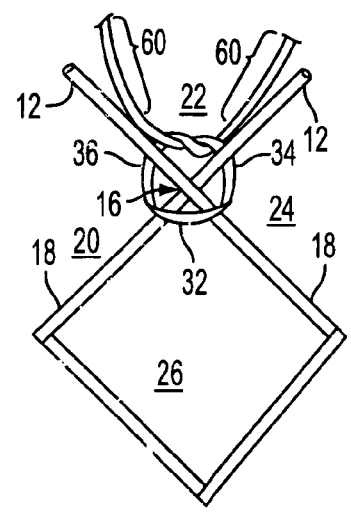
FIG. 7 illustrates one manner of joining the securing material segments depicted in FIG. 5.

FIG. 7 illustrates one manner of joining securing material segments using tying. This manner may be utilized with any of the embodiments disclosed herein. Depending on the material used for securing material 30 (which materials will be discussed below in greater detail) and/or other steps that may be taken, a traditional knot may not be needed to secure intersection 16. This is true with respect to each of the embodiments of the present methods and devices disclosed herein.

For example, the tied securing material segments 34 and 36 illustrated in FIG. 7 may be tightened, and the material used, such that the friction forces acting between the securing material segments suffice to maintain the crossed nature of strands 18. In another embodiment, a suitably biocompatible adhesive may be placed along portions of securing material segments in order to join them or in order to reinforce those that are joined, such as securing material segments 34 and 36 illustrated in FIG. 7. This may be described as gluing securing material segments together. Like gluing, heating securing material, particularly hearing securing material segments, may be used in order to join securing material segments together, or in order to reinforce securing material segments that are joined. This may be described as heating the securing material. The heating may cause some melting of the securing material. Like gluing and heating, compressing securing material, particularly compressing securing material segments, may be an effective way of joining securing material segments together, or in order to reinforce securing material segments that are joined. As used herein, to "secure an intersection" means to take steps to maintain the crossed nature of two or more crossed strands. In this regard, the precise location along each of the two or more crossed strands at which the strands are crossed need not be maintained in order to "secure an intersection."

Figure 8:
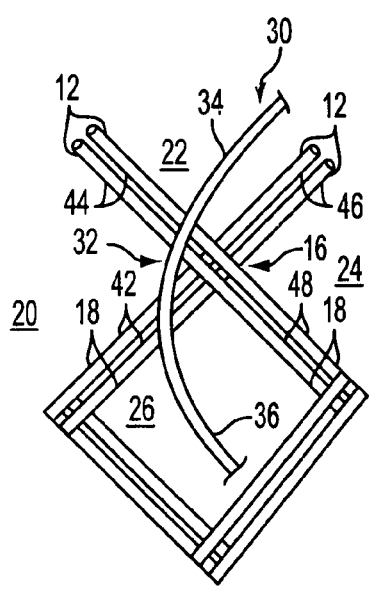
FIG. 8 illustrates yet another embodiment of a securing material passing through at least two of the sections defined by the intersection of two or more crossed strands.

FIG. 8 illustrates an alternative embodiment to those illustrated in FIGS. 3 and 5 of a step that may be used as part of the present methods. Specifically, FIG. 8 illustrates intersection 16 formed by four crossed strands 18, each have free strand end 12. Intersection 16 defines sections 20, 22, 24, and 26. Further, strand portions 42, 44, 46, and 48 illustrated in FIG. 4 are also illustrated in FIG. 8. Any two adjacent strand portions illustrated in FIG. 8 (such as 42 and 44, 44 and 46, 46 and 48, and 48 and 42) may be said to at least partially define planes as described above. Securing material 30 is illustrated in FIG. 8 as passing through sections 22 and 26. As illustrated in FIG. 8, securing material 30 is bent at location 32, thereby defining securing material segments 34 and 36 on each side of location 32. Consistent with the present methods and devices, securing material segments 34 and 36 depicted in FIG. 8 may be joined to secure intersection 16 in any of the manners disclosed herein. Similarly, joined securing material segments may be reinforced in any of the manners disclosed herein.

As used herein, "securing material" includes any suitably biocompatible material, such as nylon, wire, suture, polymer, thread, and the like. Some radio opaque securing materials that may be used include gold and platinum. These radio opaque securing materials may serve to create a visual marker useful to a surgeon during product placement within a living being.

FIGS. 9 and 10 illustrate another embodiment of a step that may be used as part of the present methods to create the present devices. FIGS. 9 and 10 are comparable in terms of views depicted to FIGS. 3 and 4 and FIGS. 5 and 6. Moreover, the only difference between the embodiment of the step illustrated in FIGS. 9 and 10 and the embodiment of the step illustrated in FIGS. 3 and 4 concerns the orientation of securing material 30. Specifically, as depicted in FIG. 9, securing material 30 has been bent, thereby forming a closed end 35 and securing material segments 34 and 36 on the sides of closed end 35. Further, securing material 30 passes through at least two of the sections (i.e., 26 and 22) formed by the crossed strands 18. More specifically, closed end 35 is depicted as crossing through at least one (i.e., section 22) of the at least two sections formed from crossed strands 18. Additionally, both securing material segments 34 and 36 are depicted as passing through at least one (i.e., section 26) of the at least two sections formed from crossed strands 18. As with the embodiment depicted in FIG. 3, it will be understood to those of skill in the art having the benefit of this disclosure that the view depicted in FIG. 9 may be characterized as being from the perspective of one looking either out through the lumen of a woven device (e.g., a stent) or into the lumen of the woven device. FIG. 10 is a side view of the securing material and intersection depicted in FIG. 9, the side view being taken from a slight perspective.

Figure 12:
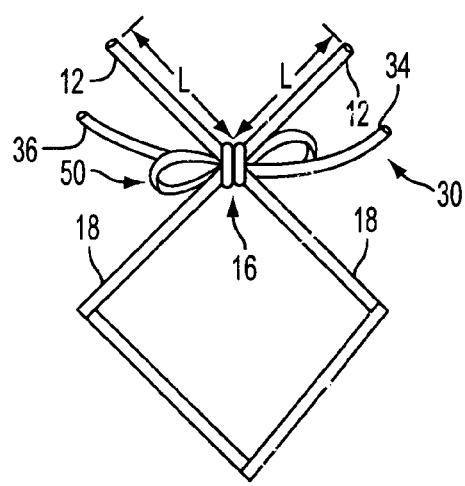
FIG. 12 depicts a knot tied in the securing material segments depicted in FIG. 11.

In FIG. 11, which depicts an embodiment of another step that may be useful with the present methods in creating the present devices, some of the elements numbers have been omitted for ease of references. FIG. 11 depicts passing securing material segments 34 and 36 through closed end 35. This step may be used to securing intersection 16 depicted in FIG. 11. Further, closed end 35 may be tightened around securing material segments 34 and 36 to further reinforce the securing intersection. Similarly, any the securing intersection may be reinforced using any other manner described herein. Additionally, securing material segments 34 and 36 may be tied in a knot 50, as illustrated in FIG. 12, to further reinforce securing intersection 16.

Turning now to FIG. 14, the securing material segments depicted in FIG. 11 are shown as being further manipulated. Specifically, FIG. 14 depicts passing securing material segments 34 and 36 through sections 26 and 22 again, such that each securing material segment depicted in FIG. 14 passes at least twice through two (i.e., 22 and 26) of the at least two sections formed by intersection 16.

Figure 13:
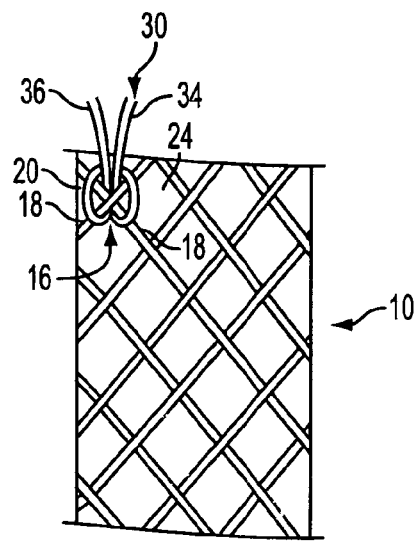
FIG. 13 depicts one of the present devices that includes a medical device having an intersection formed from at least two crossed strands, which intersection is secured with a securing material.

One of the present devices, which is suitable for implantation into a living being, is depicted in FIG. 13. Specifically, FIG. 13 depicts a body 10 having at least two strands 18 crossed to form an intersection 16, and a securing material 30 having securing material segments 34 and 36 oriented on both sides of a bent location, which securing material segments are passing through at least two (i.e., sections 20 and 24) of the at least two sections defined by intersection 16. Securing material segments 34 and 36 depicted in FIG. 13 are joined together by virtue of passing through closed end 35, which is tightened around the two securing material segments.

As with all the present methods and devices, excess securing material may be present after it is manipulated to securing an intersection. An example of such excess securing material is illustrated in FIG. 7 as excess material 60. This excess securing material may be cut in any suitable fashion. Furthermore, after an intersection is secured, in addition to cutting excess securing material, the length of free strand ends may be reduced. For example, FIG. 12 shows that strands 18 each have a segment extending away from intersection 16. These strand segments have a length L that may be reduced as desired as part of, or after, intersection 16 has been secured.

While the present disclosure may be adaptable to various modifications and alternative forms, specific embodiments have been shown by way of example and described herein. However, it should be understood that the present disclosure is not intended to be limited to the particular forms disclosed. Rather, it is to cover all modifications, equivalents, and alternatives falling within the spirit and scope of the disclosure as defined by the appended claims.

Moreover, the different aspects of the disclosed devices and methods may be utilized in various combinations and/or independently. Thus the present methods and devices are not limited to only those combinations shown herein, but rather may include other combinations. Those of skill in the art will understand that numerous other modifications may be made to the disclosed methods and devices, but all such similar substitutes and modifications are deemed to be within the scope of the claims.

I claim:

1. A method of securing an intersection formed from two or more crossed strands of a device suitable for implantation into a living being, the intersection defining at least two sections, the method comprising:
    passing a non-radio opaque securing material, which non-radio opaque securing material is separate from the two or more crossed strands, through at least two of the at least two sections, wherein the passing includes bending the non-radio opaque securing material at a location, thereby defining a non-radio opaque securing material segment on each side of the location; and
    joining the two non-radio opaque securing material segments to secure the intersection formed from the two or more crossed strands of the device suitable for implantation into a living being.

2. The method of claim 1, wherein the joining includes tying the two non-radio opaque securing material segments.

3. A method of securing an intersection formed from two or more crossed strands of a device suitable for implantation into a living being, the intersection defining at least two sections, the method comprising:
    bending a non-radio opaque securing material, which non-radio opaque securing material is separate from the two or more crossed strands, thereby forming a closed end and a non-radio opaque securing material segment on each side of the closed end;
    passing the closed end through at least one of the at least two sections;
    passing both non-radio opaque securing material segments through at least one of the at least two sections; and
    passing both non-radio opaque securing material segments through the closed end to secure the intersection formed from the two or more crossed strands of the device suitable for implantation into a living being.

4. The method of claim 3, further comprising tying the two non-radio opaque securing material segments.

5. A device suitable for implantation into a living being, the device comprising:
    a body having at least two strands crossed to form an intersection, the intersection defining at least two sections; and
    a non-radio opaque securing material that is separate from each of the at least two crossed strands and passed through at least two of the at least two sections, the non-radio opaque securing material being bent at a location and having a non-radio opaque securing material segment on each side of the location, the non-radio opaque securing material segments being joined together using one or more of tying, gluing, heating and compressing.

6. A device suitable for implantation into a living being, the device comprising:
    a body having at least two strands crossed to form an intersection, the intersection defining at least two sections, each of the at least two strands having a free end separated from the intersection by a strand segment but no other intersection; and
    a non-radio opaque securing material that is separate from each of the at least two crossed strands and passed through at least two of the at least two sections, the non-radio opaque securing material being bent at a location and having a non-radio opaque securing material segment on each side of the location, the non-radio opaque securing material segments being joined together.

* * * * *